United States Patent [19]

Comben

[11] 4,057,068
[45] Nov. 8, 1977

[54] ENCLOSURE FOR AND METHOD OF ENCLOSING A BODY IMPLANTABLE PULSE GENERATOR

[75] Inventor: Richard H. Comben, Minneapolis, Minn.

[73] Assignee: Medtronic, Inc., Minneapolis, Minn.

[21] Appl. No.: 659,650

[22] Filed: Feb. 20, 1976

[51] Int. Cl.² ............................................. A61N 1/36
[52] U.S. Cl. ............................................. 128/419 P
[58] Field of Search ........... 128/419 P, 419 C, 419 E, 128/419 PG, 419 R, 421, 422, 423; 228/25, 26, 32, 45

[56] References Cited

U.S. PATENT DOCUMENTS

| 117,770 | 8/1871 | Gulden | 228/45 |
|---|---|---|---|
| 3,658,232 | 4/1972 | Dill | 228/32 |
| 3,866,616 | 2/1975 | Purdy et al. | 128/419 P |
| 3,957,056 | 5/1976 | Comben et al. | 128/419 P |

Primary Examiner—William E. Kamm
Attorney, Agent, or Firm—Lindquist & Vennum

[57] ABSTRACT

An enclosure of the type having a plurality of members weldable to each other to enclose and hermetically seal a pulse generator. In the present invention, the members consist of first and second members or segments each having a continuous side wall with the side walls having generally circular termini of substantially equal diameter. When the sidewall termini are in abutting relation to each other, rotation of the members about the axes of the circular termini will present the entirety of the abutment to substantially the same location for sealing, as by welding, for example. One or both of the side walls may be provided with one or more recessed areas to facilitate electrical communication with the enclosed pulse generator, each recessed area being formed by a platform subtending a portion of the arc of the sidewall circular termini and a web extending between the platform and the subtended portion of the circular termini. The platform may lie entirely along a chord of the side wall circular termini or, alternatively, may include a first portion lying only partially along that chord with a second portion angularly disposed relative to a first portion and extending toward the side wall within the arc of the circular termini subtended by the chord. The platforms are provided to support electrical feedthroughs in a manner which renders them freely accessible within the enclosure without extending outwardly from the overall general dimensions of the enclosure.

7 Claims, 7 Drawing Figures

ENCLOSURE FOR AND METHOD OF ENCLOSING A BODY IMPLANTABLE PULSE GENERATOR

BACKGROUND OF THE INVENTION

Body implantable pulse generators are known to the prior art, their present principal form being the well-known cardiac pacemaker. In the body implanted environment, it is generally recognized that an enclosed and hermetically sealed pulse generator is more reliable as a result of the known and controlled environment provided by the hermetic seal which alleviates various design and performance uncertainties.

Typical prior art pulse generator hermetically sealed enclosures are formed of a plurality of weldable members with the hermetic seal being accomplished by welding the members to each other around the assembled pulse generator. To date, there are several known enclosure configurations. All enclosure configurations known to the inventor present a complex weld geometry, usually at least one weld joint which is generally rectangular having rounded corners, which results in high fabrication costs.

SUMMARY OF THE PRESENT INVENTION

The present invention provides an enclosure for a body implantable pulse generator which may be hermetically sealed with a single continuous circular weld. The enclosure is formed of two members each having a continuous side wall with each side wall having a generally circular terminus of substantially equal diameter. With the side wall termini in abutment, the enclosure may be rotated about the axes of the circular termini to present the entirety of the abutment to a single weldment location. In this manner, the enclosure of the present invention may be welded, and hermetically sealed in known manner, without the complex weld geometry of the prior art enclosures. In preferred embodiments, the present invention provides at least one platform through which feedthrough terminals may extend to provide electrical communication with the enclosed pulse generator. The platform is configured such that the terminals do not extend beyond the general overall dimensions of the enclosure while being easily accessable within the interior of the enclosure. In one embodiment, the platform is formed entirely along a chord of the circular terminus of one side wall with a web extending between the platform and side wall terminus to complete the enclosure. In another embodiment, the platform has a first portion lying along the chord of the circular terminus of one side wall and a second portion extending between the first portion and the side wall terminus, a web again extending between both platform portions and the side wall terminus to complete the enclosure. The second platform portion may be formed at an oblique angle to both the first portion and web to facilitate securement of a feedthrough terminal therein and access thereto within and without the enclosure. In any embodiment, one or both of the members forming the enclosure may be provided with one or more platforms within the sense of the present invention.

DETAILED DESCRIPTION OF THE DRAWINGS

Figure 1:
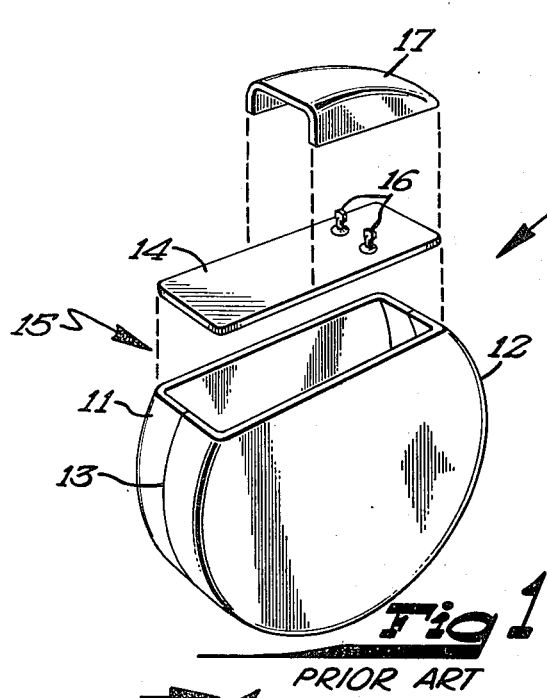
FIG. 1 illustrates one of the several prior art pulse generator enclosures.

FIG. 1 illustrates one of the several known pulse generator enclosures having the generally rectangular weld joint discussed above. The main body 10 of the enclosure of FIG. 1 is formed of first and second members 11 and 12 respectively. As illustrated, the members 11 and 12 are truncated cup-shaped members having the ends of their side wall in abutment with each other to form a first weld joint 13. To complete the enclosure, a generally rectangular plate 14 is placed over the open end 15 of the member 10 and welded in position, the weld joint being generally rectangular having rounded corners. Two feedthrough terminals 16 pass through the plate 14 to provide an electrical communication with the enclosed pulse generator. That portion of the terminal 16 on the outside of the enclosure may be connected to a lead harness or other known device by which an external lead may be placed into electrical communication with the enclosed pulse generator through the feedthrough terminal 16. A shroud 17 may be employed to protect the external lead connection and for other known purposes.

Figure 2:
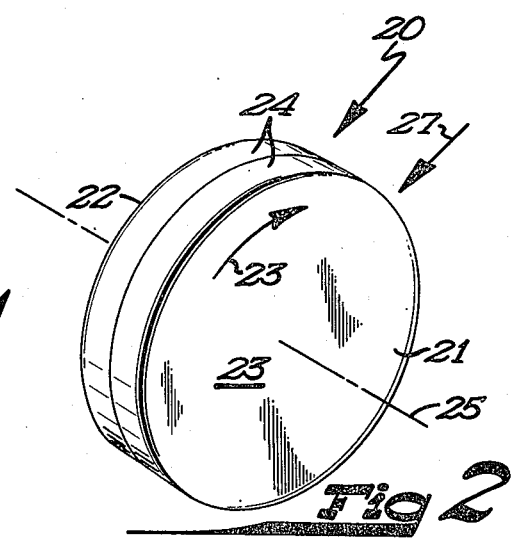
FIG. 2 illustrates the overall configuration of the enclosure of the present invention and the manner in which a hermetic seal is accomplished with a single continuous circular weld.

Referring now to FIG. 2, there is shown the general configuration of the pulse generator enclosure 20 of the present invention. Enclosure 20 is formed of first and second members or segments 21 and 22 each having a main wall 23 (one shown) and continuous side walls 24. As illustrated, the side walls 24 are generally cylindrical and have generally circular termini of substantially the same diameter. The axes of the side walls 24 and their circular termini coincide and are illustrated by the line 25 through the main walls 23. By rotating the enclosure 20 about the axes 25, the entirety of the abutment of the sidewalls 24 may be presented to a single location. For example, by rotating the enclosure 20 in the direction indicated by the arrow 26 for one complete revolution, the entirety of the abutment between the sidewalls 24 will have passed the location indicated by the arrow 27. With known welding equipment operating at the point indicated by the arrow 27, the entirety of the abutment of the sidewalls 24 can be welded with only a simple rotational motion being required. The welding may be effected through electron beam or any other welding technique. Members 21 and 22 may be of any weldable material capable of withstanding the environment and providing the desired sealing, titanium, for example.

Figure 3:
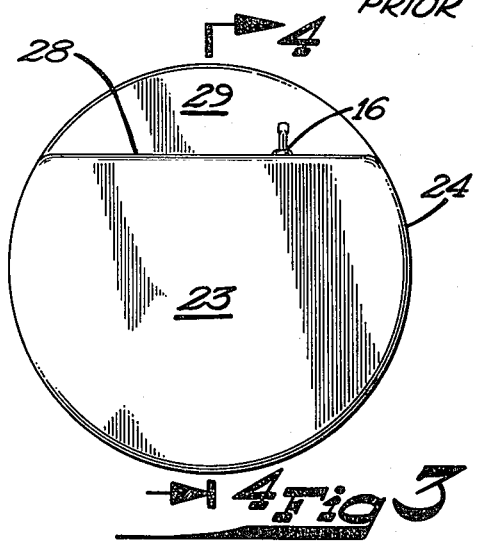
FIG. 3 illustrates a side view of a preferred embodiment of the invention illustrated generally in FIG. 2.
Figure 4:
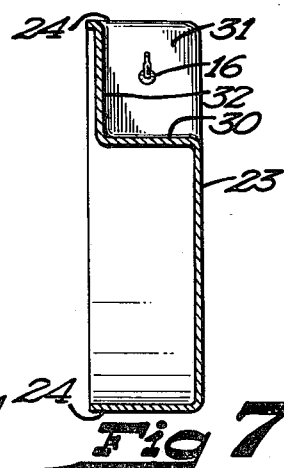
FIG. 4 illustrates a cross-section taken through the line 4—4 in FIG. 3.

As stated above, FIG. 2 illustrates the general overall configuration of the enclosure 20 of the present invention. FIG. 3 illustrates a preferred embodiment of one or both of the members 21 and 22 which makes special provision for an electrical communication with the enclosed pulse generator without effect on the circular abutment of the side walls 24. As shown in FIGS. 3 and 4, at least the terminus of the side wall 24 is continuous and circular while the main wall 23 is truncated. A platform 28 subtends a portion of the arc of the sidewall 24 terminus and, in the illustrated embodiment, extends from one end of the arc to the other along a chord of the circle formed by the side wall 24 terminus. A web 29 extends between the platform 28 and the terminus of the sidewall 24 to complete the enclosure.

The platform 28 is provided to allow a feedthrough terminal 16 to pass through the sidewall 24 while the terminal remains within the general overall configuration of the enclosure 20. That is, the feedthrough terminal 16 lies within a volume which would be included within the enclosure if the sidewall 24 were cylindrical in its entirety and the platform 28 and web 29 were omitted. In this manner, electrical communication with the enclosed pulse generator may be provided without significant projection of a terminal, or other connecting member, beyond the general enclosure configuration. Of course, in some circumstances it may be desirable to have the terminal project beyond the general enclosure configuration in which case the terminal 16 may be elongated without departure from the scope of the present invention.

The feedthrough terminal 16 illustrated in FIGS. 3 and 4 may be identical to those known to the prior art and discussed with reference to FIG. 1, as may be all of the feedthrough terminals of like reference number discussed herein. Also, FIGS. 3-7 show only a single feedthrough terminal for the purpose of illustrating the cooperation between the terminal 16, the sidewall 24 and the various platforms and webs to be described herein. Any number of feedthrough terminals 16 may be employed within the embodiments of the present invention consistent with available space and the number necessary for the application in question.

Figure 5:
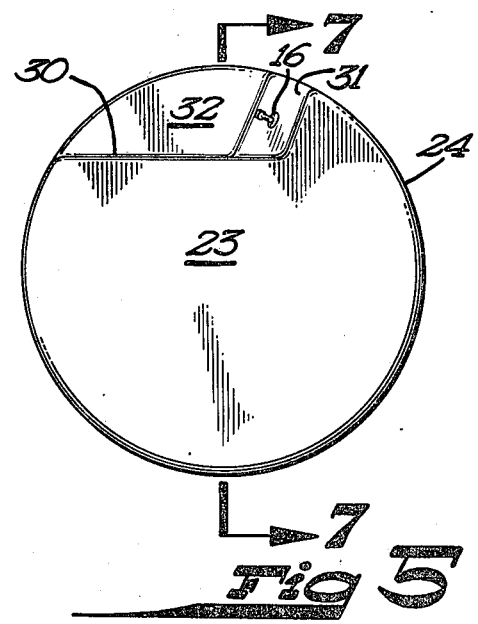
FIG. 5 illustrates a side view of another preferred embodiment of the invention illustrated generally in FIG. 2.
Figure 7:
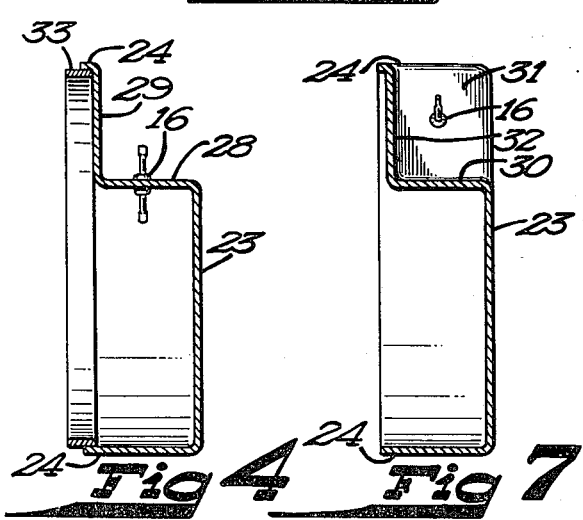
FIG. 7 shows a cross-section taken along the line 7—7 in FIG. 5.
Figure 6:
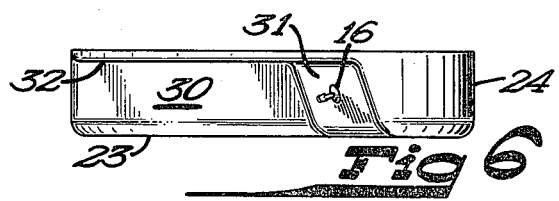
FIG. 6 shows a top view of the embodiment of FIG. 5.

Referring now to FIGS. 5-7, there is illustrated another preferred embodiment of one or both of the members 21 and 22 with special provision being made for electrical communication with the enclosed pulse generator without effect of the generally circular weld joint provided by the sidewall 24 termini. In the embodiment of FIGS. 5-7, the terminus of the side wall 24 is continuous and circular. The platform of the embodiment of FIGS. 5-7 is formed of a first portion 30 lying along a chord of the circle formed by the terminus of the side wall 24 and a second portion 31 angularly disposed relative to the first portion and extending from the first portion toward the terminus of the side wall 24 within the arc of the circle formed by the terminus of the side wall 24 subtended by the chord along which the portion 30 lies. A web 32 extends between the platform portions 30 and 31 and the terminus of the side wall 24 to complete the enclosure. As illustrated, the platform portion 30 and web 32 are generally perpendicular to each other and the platform portion 31 forms an oblique angle with both the platform portion 30 and web 32 for reasons to be described more fully below. A feedthrough terminal 16 extends through the platform portion 31 to provide an electrical communication with the enclosed pulse generator with the external portion of the feedthrough terminal 16 lying within the general overall configuration of the enclosure. In some instances it may be desirable to have the feedthrough terminal 16 in the embodiment of FIGS. 5-7 project beyond the overall configuration of the enclosure. In such instances, the feedthrough terminal 16 may be elongated to provide the desired projection without departure from the scope of the present invention.

As described above, the platform portion 31 forms an oblique angle with both the platform portion 30 and the web portion 32. Alternatively, the platform portion 31 may form an oblique angle with the platform portion 30 but be perpendicular to the web 32. It has been found, however, that securement of the terminal 16 within the platform portion 31 is more readily accomplished when the platform portion 31 is obliquely disposed relative to the web 32, as illustrated. In addition, the oblique arrangement of the platform portion 31 angles that portion of the feedthrough terminals 16 within the enclosure away from the main wall 23 thereby facilitating electrical connection between the pulse generator to be enclosed and the feedthrough terminal 16. While only one feedthrough terminal 16 is illustrated in the embodiment of FIGS. 5-7, and that terminal passes through the platform portion 31, it is to be understood that any number of terminal 16 may be employed within either of the platform portions 30 and 31 consistent with the space available and the number of terminals necessary for the desired application.

Any of the members illustrated in FIGS. 3-4 and 5-7 may be employed interchangeably with themselves or each other they or may be combined with a member having a side wall which is cylindrical in its entirety (having no platform or web). In any combination, it is intended that at least the termini of the side walls 24 be circular and of approximately the same diameter such that the termini will abut with each other. In this manner, any of the illustrated or described embodiments may be interchangeably combined while still presenting the entirety of the abutment to the same weldment location with a simple rotational movement. Of course, the welding action will be directed at the outer surface of the sidewalls 24. Recitations that "the abutment" or "the entirety of the abutting surfaces" are presented to the same location are intended to embrace this fact. To facilitate the welding operation, a retaining ring 33 (see FIG. 4) may be used with any of the embodiments illustrated or described in a manner known to the prior art.

Obviously many modifications and variations of the present invention are possible in light of the above teachings. For example, a shroud such as that illustrated at 17 and FIG. 1 may be configured to overlie the recessed areas described herein for reasons well known to the prior art. Also, the terminals 16 may be secured within either of the webs 29 or 32, if desired. In addition, in the embodiment of FIGS. 5-7 the web 32 and platform portion 30 may be combined into a single arcurate web surface with the terminals 16 extending through the platform portion 31. It is therefore to be understood that, within the scope of the appended claims, the invention may be practiced otherwise than as specifically described.

I claim:

1. In an enclosure for a body implantable pulse generator of the type having a plurality of members weldable to each other to enclose and hermetically seal said pulse generator and having feedthrough means passing through said enclosure, the improvement wherein said plurality of members comprises first and second members each having a continuous side wall terminating at continuous generally circular means of substantially equal diameter, at least one of said side walls including platform means subtending a portion of the arc of said circular means and web means extending between said platform means and said subtended arc portion of said circular means, and said feedthrough means passing through at least one of said platform means and web means.

2. The enclosure of claim 1 wherein at least a portion of said platform means lies along a chord of said circular means.

3. The enclosure of claim 1 wherein the entirety of said platform means lies along a chord of said circular means.

4. The enclosure of claim 1 wherein said platform means lies along the chord of said circular means which subtends said arc portion.

5. The enclosure of claim 1 wherein said platform means comprises a first portion lying along a chord of said circular means and a second portion angularly disposed relative to said first portion and extending from said first portion toward said circular means within the arc of said circular means subtended by said chord, said feedthrough means passing through said platform means second portion.

6. The enclosure of claim 5 wherein said web means is generally parallel to the plane of said circular means, said first platform means portion being generally normal to said web means and said second platform means portion forming an oblique angle with both of said web means and said first platform means portion.

7. The method of enclosing and sealing a body implantable pulse generator comprising the steps of: forming first and second enclosure segments each having a main wall and a continuous side wall with the side walls terminating at continuous generally circular mating surfaces equidistant from an axis through the main wall of their respective segments, said forming step further comprising the step of forming platform means and web means within the side wall of at least one of said enclosure segments while maintaining the continuity of said mating surfaces, said platform means subtending a portion of the arc of said circular mating surface and said web means extending between said platform means and said subtended arc portion of said mating surface;

passing feedthrough means through one of said platform means and web means;

placing the mating surfaces in abutting relation; and rotating said segments about said axes to present the entirety of said abutting mating surfaces to substantially the same sealing location.

* * * * *